(12) United States Patent
Eck

(10) Patent No.: US 8,097,461 B2
(45) Date of Patent: Jan. 17, 2012

(54) INTERFERENCE CONTROL PANEL FOR EVALUATION OF ANALYTICAL ASSAYS FOR SAMPLES DERIVED FROM BLOOD

(75) Inventor: Michael J. Eck, Walnut Creek, CA (US)

(73) Assignee: Life Technologies Corporation, Carlsbad, CA (US)

( * ) Notice: Subject to any disclaimer, the term of this patent is extended or adjusted under 35 U.S.C. 154(b) by 760 days.

(21) Appl. No.: 11/941,017

(22) Filed: Nov. 15, 2007

(65) Prior Publication Data

US 2009/0130653 A1    May 21, 2009

(51) Int. Cl.
*G01N 33/53* (2006.01)
*G01N 31/00* (2006.01)
(52) U.S. Cl. ........... 436/8; 435/7.1; 435/7.21; 436/1; 436/501; 436/518; 424/9.1; 424/520; 530/300; 530/350
(58) Field of Classification Search .............. None
See application file for complete search history.

(56) References Cited

OTHER PUBLICATIONS

Goce Dimeski, Interference Testing, Clin Biochem Rev vol. 29 Suppl (i) Aug. 2008 I S43-S48.*
Tate and Ward, Interferences in Immunoassays, Clin Biochem Rev vol. 25 May 2004 105-120.*

* cited by examiner

*Primary Examiner* — Lisa Cook

(57) ABSTRACT

The invention relates to quality control of analytical assays, particularly NAT assays of blood samples containing nucleic acids. A control panel containing quantified amounts of substances known to interfere with an analytical assay is used and compared with a reference sample in the analytical assay. A comparison of the assay results interference panel validates the assay and can serve as a periodic quality control check for the analytical assay as well as related methods and protocols. The use of the control panel of the invention can also determine whether interfering substances are present and establish under what conditions the analytical assay reliable.

26 Claims, No Drawings

INTERFERENCE CONTROL PANEL FOR EVALUATION OF ANALYTICAL ASSAYS FOR SAMPLES DERIVED FROM BLOOD

BACKGROUND OF THE INVENTION

Blood samples are extensively used for clinical diagnosis and in medical research. In many assay formats, the presence of certain components in blood can interfere with the assay and render the test results unreliable or unusable. Interference is typically manifested as an inhibition of chemical reactions in the assay that reduces the performance and compromises the integrity of the assay and its result.

Patient samples may be compromised in a clinical setting by conditions such as poor handling, haemolysis, icterus, or lipemia. It is for example well known that HIV patients, treated with protease inhibitors, often show increased triglyceride levels. Yet another example of a compromised sample is cadaveric samples, which are often tested before organ transplantation. Cadaveric samples can be very challenging for nucleic acid tests, due to their potentially inhibitory nature from lysed or degraded tissues.

Blood samples, or samples derived from whole blood, are often analyzed for a nucleic acid analyte by the Polymerase Chain Reaction (PCR), other Nucleic Acid Amplification Technologies (NAT), or other nucleic acid detection technologies. NAT and PCR-based diagnosis of disease, infections, and genetic variations, as well as forensic analysis and blood typing are well known. It is also known that contaminants or PCR inhibitory substances such as lipids, hemoglobin, bilirubin or frequently administered drugs and anticoagulants can interfere with the PCR assay.

PCR-based assays rely on amplification and detection of nucleic acids present in the blood samples. These reactions can be dramatically reduced or blocked by the presence of contaminants or natural components of blood that inhibit chemical or biochemical reactions that occur in the assay. Blood components known as PCR inhibitors include immunoglobulin, heme, hemoglobin, leukocyte DNA, and common blood additive such as the anticoagulant heparin. Therefore, the usefulness of PCR-based detection of microorganisms, pathogens and other targets in complex biological samples, such as clinical, environmental, and food samples, is limited in part by the presence of substances that inhibit the fundamental amplification reaction at PCR or which reduce the amplification efficiency.

Because the potential for contamination and interference in PCR-based assays is well known, a variety of different approaches have been studied to attempt to prevent the inhibition. In one approach, the inhibition caused by specific substances is tested to attempt to compensate for their presence in a test sample or assay.

Solutions that samples used for assays typically are, or may be, converted into a liquid form containing compounds that inhibit chemical or biochemical reactions in an assay. The agents that cause interference or inhibition in the inhibitory testing assay include: hemoglobin, L-ascorbic acid, free fatty acids, iron, heme, triglycerides, drugs, bilirubin, conjugated bilirubin, bicarbonate, pH extremes, proteins, bile acids, larger amounts of DNA, or keto-acids. These inhibitors may interfere with cell lysis, degrade or capture of the nucleic acids, inactivate Taq polymerase or degrade the specificity of this enzyme, or otherwise interfere with enzymes used in nucleic acid amplification or detection technologies. In particular reverse transcription PCR (rt-PCR), which initially reverse transcribes RNA into cDNA, is very sensitive to the presence of inhibitors. In an attempt to preserve the fidelity of the assay, different methods of sample preparation have been developed to remove the inhibitory effect of these blood-derived components.

It is possible to attempt to control for inhibitory substances by monitoring the presence or absence of PCR product(s) at the end of thermal cycling by gel electophoresis, dot blots, high-pressure liquid chromatography or microtiter or plate-based, calorimetric assay. The quantitative effect of inhibitors on DNA synthesis can also be studied by measuring the efficiency of incorporation of radiolabeled nucleotides. Recently, thermal cyclers with real-time detection of PCR product accumulation were introduced, offering a new possibility to study amplification efficiency and/or DNA synthesis efficiency. Most commonly a known amount of an internal control molecule, which should behave similar to the target, is added into each PCR reactions. A change from the expected signal generated by the internal control can indicate the presence of inhibitors but can also change if the assay was not performed correctly. An internal control used for quantification is sometimes referred to as Quantification Standard (QS).

A resolution of the problem of inhibiting substances in assays can be attempted by sample preparation techniques. PCR-inhibitory components include salts, complex polysaccharides, heme protein in blood, RNases, DNases, feces, some detergents (e.g., SDS), DNA intercalating substances (e.g., intercalating dyes), humic substances in soil, melanin, collagen, myoglobin, alcohol, calcium ions, lactoferrin, proteases, proteinases in milk, and urea in urine. Significant effort is being devoted to the development of sample preparation methods to remove these substances and overcome the problems of inhibition in the reactions that occur in an assay. Different processing techniques are also being employed to reduce the effect of inhibitors. For example, aqueous two phase-systems, boiling, density gradient centrifugation, dilution, DNA extraction methods, enrichment media, filtration, and immunological techniques have been used to attempt to avoid the effect of inhibitory substances in PCR analyses. The thermostable DNA polymerase is perhaps the most important target site of PCR-inhibiting substances. The most widely used polymerase in PCR-based methods for the detection of microorganisms is Taq DNA polymerase from *Thermus aquaticus*. Other DNA polymerases with manganese instead of magnesium as cofactor are commonly used for rt-PCR. Other systems use a reverse transcriptase in combination with a DNA polymerase for rtPCR. Taq DNA polymerase, as well as many other PCR enzymes, can be degraded by proteinases, denatured by phenol or detergents, and inhibited by blocking of the active site by the inhibitor, which is the effect of the heme protein. Inhibitors can also work on the substrate by decaying DNA or RNA. RNases in plasma are known to destroy RNA, or DNases can destroy DNA.

One approach for quality control of analytical assays is to use a sample-processing control as an internal control to verify adequate processing of the target analyte. This monitors the presence of inhibitors to avoid a false negative result, or incorrect quantification. If the system fails with this control, then there is an invalid result.

While common interfering substances are well known, it remains difficult and inconvenient to prepare constant, quantified controls for analytical assays. The reliability of standard solutions may be questionable or concentrations may not be calculated correctly. Also, it is time-consuming to be constantly preparing standards and calibrating them from week to week. This is particularly true for clinical samples, where there is high volume of testing, yet these are samples which must conform to rigorous quality control standards. Further, patient samples may be contaminated, or be presented in less than optimum condition. Because sample size and availability may be limited, however, it is often important that these critical samples be accurately analyzed.

Known guidelines recognize two primary limitations of interference testing. Properties of compounds added to a serum pool may be different from those of the compound naturally circulating in vivo. Also, the presence of more than one interfering substance may offset or enhance the concentrations of interfering substance and analyte tested. Various combinations of interfering substances in various combinations, therefore, should be evaluated in an assay.

To assure optimum performance of the analytical assay, a test assay includes several types of controls in addition to the test sample. A negative control, usually with a key ingredient missing, indicates a positive test result can be trusted. A positive control, usually a known amount of the analyte of interest, indicates the assay is functional. An internal control has a known substance added to the test sample before analysis, while an external control compares the test sample with other samples of substances run in the same assay. Because analytical assays can be sensitive and are designed to detect very small quantities of analyte, it is very important to include complementary controls to evaluate an analytical assay for acceptance criteria.

Accepted guidelines for estimation of interference characteristics recommend evaluating the effect of potentially interfering substances added to the sample of interest, as well as evaluating the bias of individual patient specimens in comparison to a highly specific comparative measurement procedure (Clinical and Laboratory Standards Institute. Interference Testing in Clinical Chemistry; Approved Guideline—Second Edition, 2005, p. 13). An interference screen can be prepared by adding a potentially interfering substance to a sample pool and evaluating bias relative to a control portion of the same pool, which is termed paired-difference testing. An interference screen, with many substances at relatively high concentrations, simulates interference and provides a standardized evaluation to complement actual patient samples.

It would be very useful to have calibrated substances prepared in an interference panel to determine the presence of interfering substances and to evaluate the performance of an analytical assay. This would also allow the standardized comparison of interfering substances on different assays or diagnostic systems.

SUMMARY OF THE INVENTION

The invention provides a panel of calibrated substances known to have the potential to interfere with an assay of interest. The assay measures substances in plasma or blood-derived samples. A known quantity of an analyte of interest is added to members of the panel and then tested in the assay. In a preferred embodiment, the interference panel is used in Nucleic Acid Detection assays including a nucleic acid extraction and amplification analytical assay. The analyte of interest may be extracted from serum, plasma, whole blood or other blood fraction.

The members of the interference panel are substances chosen to mimic potential interfering substances or clinical conditions that could adversely affect the analytical assay. These could include haemolysis, icterus, lipemia, or frequently administered drugs or anticoagulants, such as heparin. The panel is designed to test the limits of the assay system to validate the assay thereby confirming that assay results are accurate and reliable, under conditions in which the sample itself may not be optimal. The interference panel monitors the effectiveness and efficiency of the extraction, amplification and detection of the target analyte in the presence of a defined amount of a potential inhibitor. The panel allows determining which potential inhibitor interferes at which level with an assay. This information can be used to set acceptance criteria or warn the user of this assay e.g. in the package insert about possible problems in case this inhibitor is present above a certain level. Further the panel can be used to validate, verify or otherwise confirm that an assay system is performing consistent with its design by performing the assay in the presence of a known amount of inhibitors.

The panel members are provided in standardized vial volumes at known concentrations. The analyte of interest is spiked into each panel member at various known concentrations, and each sample is analyzed within the reportable dynamic range of the assay. The level of interference caused by the interference panel member can be quantified by recording and analyzing the extent to which the interference affects the performance of the assay, for example, the delay in threshold cycles of the PCR reaction, or the decrease in quantity of product in the presence of the interfering substance. The concentration of potential inhibitor can be modulated by adding the target analyte (e.g. a virus) in different volumes. Adding 100 μL of a non-inhibitory liquid containing a certain number of viruses into the vial containing the potential inhibitor would dilute the potential inhibitor more than the same number of virus added in a 10 μL volume of a non-inhibitory liquid.

The method of the invention includes performing an assay in the presence of potentially interfering substances and determining the extent of interference, typically by comparing the results to evaluate quality and performance of an assay, to verify or quantify interference effects, or to confirm observed interference in patient samples. The panel of the invention can be applied to custom design assays, and verification of assay of off-the-shelf performance. By comparison of the reactions of the test sample, the normal plasma sample and the panel members, the panel can also determine the acceptable levels of interfering substances for test results.

The inhibition panel of the present invention contains potentially interfering substances that frequently occur due to clinical conditions such as haemolysis, icterus, or lipemia, cadaveric samples, or due to administered drugs or anticoagulants such as heparin. The level of interfering substance in each panel member is within the range of typically occurring human specimens. The panel may also contain a normal reference matrix (EDTA plasma), which can be used as a baseline for comparison. The interference panel can also include common blood-borne viruses, such as HCV and HBV, and different internal controls spiked into each panel member in equal quantities.

DETAILED DESCRIPTION OF THE INVENTION

The invention provides a method of detecting inhibition that may be observed in analytical assays as the result of interfering substances commonly found in serum, plasma or whole blood specimens. The members are designed to mimic the potential interfering inhibitor components substances and clinical conditions, such as haemolysis, icterus, and lipemia, and also contains representative substances that are frequently used as drugs or anticoagulants (such as heparin) which may cause inhibition of certain assays.

As an external quality control, the inhibition panel provides a method to test the detection and sensitivity limits of an analytical assay system and determines whether a subject assay can report proper results under conditions in which the sample is not optimal. The inhibition panel also verifies the effectiveness of any sample preparation or extraction method and screens for the presence or absence of suspected inhibitors in an analytical assay or system after sample preparation. Further, it allows a standardized check that internal controls or QS are able to indicate the presence or absence of an inhibitor.

As part of a discrete method for assay evaluation, the inhibition panel evaluates the efficiency of the extraction methodology, to determine that extraction methods or assay systems functionally eliminate any specific inhibitors that may be present with analytes found in whole blood and plasma.

As part of a discrete method for extraction or system evaluation, the inhibition panel verifies that a methodology utilized in sample preparation has effectively eliminated the inhibitors or interfering substances so that instruments are validated according to Clinical Laboratory Improvement Amendments (CLIA) regulations.

The inhibition panel and assay of the present invention can also validate or verify the performance of a certain assay technique, platform or kit such that when a sample of known concentration is spiked into each panel member, panel members are analyzed in parallel and the quality or performance of the assay can be determined. For example, PCR results are evaluated to determine whether or not the amplification reaction occurring in each panel member shows any difference from the non-inhibitory reference control typically used in the assay. Thus, inhibiting or interfering substances that are present in whole blood or plasma are detected by comparison of the separate data generated from the reaction that occurs for each panel member and with the reference plasma sample.

Assays that rely on the binding reaction between an antigen and an antibody are known as immunoassays and are often used for diagnostic purposes. As used herein, "immunoassay" includes methods which utilize the antibody and a label to detect an antigen in human body fluids, cell or tissue extracts. Other immunoassay-based diagnostic techniques include competitive binding assays, direct, indirect or double antigen sandwich assays (e.g. for the detection of antibodies directed against infectious disease pathogens) and immunoprecipitation assays [Zola H., Monoclonal Antibodies: A Manual of Techniques, CRC Press, Inc. (1987) pp. 147-158]. Antibodies used in diagnostic assays are typically labeled with a detectable moiety, which can be a radioisotope, a fluorescent or chemiluminescent compound used in conjunction with an enzyme-linked antibody. In the case of double antigen sandwich assays, the antibody binding antigen is labeled.

Antibodies which specifically bind blood-derived antigens are particularly useful in assays for the diagnosis of conditions or diseases characterized by altered expression of proteins in the body. Immunoassays are also used to monitor the progress of disease, detect pregnancy, detect infections and several other important diagnostic goals. Immunoassays are subject to inhibition by any substance that interferes with the highly specific binding event between an antibody and antigen. The reaction site in an antibody or antigen reaction is highly sensitive and depends on the affinity of the antibody. The verification or validation of an assay or the identification of an inhibitory substance is achieved by testing members of the inhibition panel in an immunoassay wherein the inhibition panel members are reacted with a quantity of the antigen and antibody. The extent to which the binding reaction is inhibited can be detected and analyzed in the same manner as is described elsewhere herein to correlate the inhibitory substance to the reaction between the antibody and the antigen for which the antibody is specific and to evaluate the quality and performance of an immunoassay.

The use of the inhibition panel also permits comparison and evaluation of entire systems, providing the opportunity to evaluate and choose the best assay protocols or protocol a system. Furthermore, the inhibition panel permits the evaluation of the characteristics of a sample source such that limits of other parameters can be assigned to patient samples to set any requirements for testing, e.g., a maximal level of hemoglobin or heparin may be set for sample acceptance.

The components of the inhibition panel of invention are preferably derived from whole blood or blood derivatives. In some panel members, human plasma is combined with an interfering substance at a level appropriate to mimic naturally occurring patient specimens. The inhibition components may include different kinds of plasma, serum, or other cell-free derived components of whole blood. The components may be derived from either fresh blood, frozen blood or from cadaveric blood samples.

A possible source of cadaveric samples is blood drawn from a cadaver before embalmment. Blood of dead animals (e.g. pigs, bovine, other mammals or birds) could possibly serve as an alternative source to human cadaveric blood. Another alternative to cadaveric samples is collecting human whole blood and letting it sit for extended period of time to simulate body decay before formulation of a product. A possible cause for the inhibition of cadaveric samples is the presence of heme and DNA, both released after lysis of blood cells. This scenario can be mimicked by e.g. partially or fully lysing donated whole blood (whole blood lysate) or mixing plasma with DNA and hemoglobin or heme or iron or lysed red blood cells at physiological levels.

The interfering effects of such substances on general NAT and EIA assays has been established and documented. It is critical to consistently monitor the effect of such interfering substances in the performance characteristics of the assay validated by the end user. This is especially true of Analyte Specific Reagents (ASRs) and homebrew assays, where no data is available to verify the performance of the assay in the presence of such substances. The use of a standardized interference panel allows direct comparison of interference data in different settings.

The invention can be used to evaluate any sample preparation platform (extraction step, including sample purification and concentration) and subsequent analytical assay (such as real-time PCR). The volumes of the final samples spiked with the analyte and/or the final concentrations of the analyte may be adjusted by the end user so that they are within the recommended levels for the assay of interest. The frequency of the usage is determined by the end user, and will depend upon evaluation requirements of the individual laboratory.

The components described are formulated to mimic normal human specimens containing naturally occurring interfering substances, including interfering substances due to medication, or interfering substances introduced during routine blood collection processes.

The panel can be designed for use with any assay system used to detect a broad number of analytes derived or stored in whole blood or blood derivatives. Further, the concentrations of each potentially interfering substance used as a member of the panel can be varied, i.e., from low to medium to high concentrations in panel members to establish a broad range of testing parameters or to establish discrete levels of inhibition for testing or comparison. Accordingly, the levels of interfering substances present in each panel member can be determined to be within the range observed in clinical patient specimens that are tested for many different analytes.

Although there is a flexibility in the type of analytes which may be used with the panel, all inhibition components, including the non-inhibitory reference sample, should be spiked with an equal volume (and concentration) of the desired analyte, so that the interference/non-interference claims of the extraction and/or assay system are consistently evaluated. One or more user defined non-inhibitory reference samples can be used in conjunction with, or can replace a non-inhibitory reference sample if one is provided with the inhibitory panel members.

The following Examples 1-6 describe preparation of representative interference panel members to use in the method of the invention. Examples 7-8 describe the practice of embodiments of the invention where the inhibition panel is used to evaluate an assay. As used herein, the term "evaluation" means to assess the reliability of an assay in the presence of potentially inhibitory substances including verification of performance or accuracy or confirmation of any aspect of assay performance or reliability. This includes assay validation, verification of the reliability, consistency, reproducibility, quality, and performance characteristics of an assay, including non-clinical performance studies.

Example 1

Manufacture of 10% Hemoglobin Solution

Appropriate safety procedures were followed to avoid transmission of blood-borne infections. Lyophilized human hemoglobin was dissolved in 1×TNE buffer (10 mM Tris, 0.2M NaCl, 1 mM EDTA, pH 7.4) to prepare a 10% solution. Extreme caution was utilized in the handling of lyophilized hemoglobin because it is electrostatic and easily dispersed. The solution was stirred for at least 30 minutes at room temperature, and tested using a spectrophotometer (such as the spectrophotometer sold under the name HemoCue®, or the equivalent).

Example 2

Manufacture of 1%, 2% and 4% Hemolyzed Plasma Panel Members

The dilution factor was calculated for the volume of hemolyzed plasma required. The appropriate amount of 10% hemoglobin was measured to give 1%, 2% or 4% concentration of hemoglobin. The volume of NAT-DM EDTA diluent was calculated. Both diluents and analyte stocks were measured gravimetrically, assuming a density of 1.0 g/ml. The desired volume of diluent was added to a container, and the desired volume of 10% hemoglobin was added. A lid was placed on the container, and the solution stirred slowly for 30 minutes or until completely mixed at room temperature. The solution was tested with a spectrophotometer (HemoCue®) to verify the hemoglobin concentration was within 10% of the desired concentration. The solution was stored at 2-8 degrees C. and used within one week of preparation.

Example 3

Manufacture of Concentrated Fatty Plasma (Cold Fat Depletion)

Concentrated fatty plasma may be prepared by extraction of triglycerides from cold fat by the following process:

A water bath was filled with distilled $H_2O$, then adjusted to 37° C. Bags of cold fat were allowed to thaw for 30 minutes in the 37° C. water bath. Once the plasma bags were thawed and no apparent cryoprecipitate are visible, the plasma bags were placed on a bench toweled flat surface to absorb excess moisture. The plasma bags were selected based on the coloration. The plasma bags were inspected and placed on white paper then visually evaluated by assessing the clarity and the obscurity of the plasma bag under the follows criteria:

| | | |
|---|---|---|
| i. | Pale green to dark yellow | plasma is high in fat |
| ii. | Light yellow to white | plasma is above average fat |
| iii. | Orange-yellowish gold | plasma has low fat content |

Four plasma bags of 300 mL fill volume each were chosen and hung hooks customized for plasma bag holes. Using a tubing connected with a needle or pointed syringe adapter, the septum opening was cut and a tube was inserted that is attached by a needle inside the bag opening.

300 mL centrifuge containers were filled with plasma from the bags by attaching the end of the tube running from the plasma bag into the centrifuge container, and without overfilling, the centrifuge tube was filled to about 255 mL. The 4 plasma bags permitted about five 300 mL centrifuge containers to be filled to about 255 mL per container. After the volume of plasma was collected, it was placed in a 4° C. refrigerator for 2 hours to cool. The containers were centrifuged at 20,000×g (RCF) at a temperature setting of 4° C. for an hour. The liquid phase (supernatant) from the opposite side of the container from where the fat bodies have adhered was carefully decanted and the fat was carefully pipetted out. At this point of the process, some of the fat adhered to the side of the container as well as floated to the top of the supernatant, due to the low density of the fat to plasma liquid density.

A second ultracentrifugation was performed at 20,000×g (RCF) at a temperature setting of 4° C. for an hour. The liquid (supernatant) was decanted and carefully pipetted to remove the fat as above. The supernatant was started in 2-8° C. refrigerator overnight. The following day, if there was further separation, the residual supernatant was decanted to transfer the fat to a container and placed in short-term storage at 2-8° C. To save the remaining liquid (supernatant) of the plasma, the residual supernatant was kept at 2-8° C., or the fat was concentrated by performing the process as described above. The level of triglycerides in this concentrated fatty plasma was measured. Lipemic plasma was diluted with normal human plasma so that the final concentration of triglycerides was 3000 mg/dL.

Example 4

Manufacture of Lipemic Human Plasma

The volume of lipemic human plasma required was calculated. The required volume of lipemic plasma was added to a container. Sodium azide was added to 0.05%, and gentamicin was added to 0.05%. The solution was stirred slowly at 2-8 degrees for 15 to 20 minutes, or until the preservatives were completely dissolved. The solution was stored at 2-8 degrees C., and used within 30 days. The material may be stored at −20 degrees C. for up to one year.

Example 5

Manufacture of Icteric Plasma (1× Bilirubin, 0.03%)

The volume of 1× bilirubin, 0.03% (icteric plasma) was calculated using a stock of 10× bilirubin 0.3%. Autoclaved DI water was added to a container. 1 N NaOH was added in equal mass to the amount of 10× bilirubin, 0.3% that was subsequently added. A lid was placed on the container, and the solution stirred slowly with an autoclaved stir bar for 30 minutes at 2-8 degrees C. An equal mass of NAT-DM EDTA (citrated) was added, and the solution mixed slowly for 15-20 minutes at 2-8 degrees C. The pH was measured to determine that the pH ranged from 7.5 to 8.0. The solution was stored at 2-8 degrees C.

Example 6

Manufacture of Heparinized Human Plasma

Heparinized human plasma was added to a container. The volume was made 0.05% sodium azide and 0.05% gentamicin sulfate. Caution was taken to wear a dust mask when handling gentamicin sulfate. A lid was placed on the container, and the solution stirred slowly at 2-8 degrees C. for 15-20 minutes or until the preservatives were completely dissolved. Heparinized human plasma was stored at 2-8 C and used within 30 days of preparation. Alternatively, it may be stored at −20° C. for up to one year.

Example 7

Preparation of Panel Members and Analyte Mixtures

Panel members were chosen according to the inhibitory substances to be tested and at various concentrations. For example, an inhibition panel was prepared for the following panel members: EDTA plasma (negative control), haemolyzed blood (low concentration), haemolyzed blood (middle concentration), haemolyzed blood (high concentration, heparinized plasma, lipemic plasma, and icteric plasma (see Table I).

The inhibition panel members were thawed at 37° C. for 15 to 20 minutes, vortexed vigorously to form homogenous suspensions of panel members and eliminate any precipitates that may form in panel members that contain viscous substances such as haemoglobin or lipids. Any unused portions were returned to the recommended storage conditions immediately following use. Each panel member sample was provided in approximately 2 mL vials.

TABLE 1

Interference Panel Members

| Panel Member | Description |
| --- | --- |
| 1 | EDTA Plasma Negative |
| 2 | Haemolyzed Blood, Low |
| 3 | Haemolyzed Blood, Mid |
| 4 | Haemolyzed Blood, High |
| 5 | Heparinized Plasma |
| 6 | Lipemic Plasma |
| 7 | Icteric Plasma |

The analyte of interest was then spiked into each panel member. The analyte of interest was in a physiological buffer, plasma, serum or other blood derivative that is compatible with the Inhibition Panel members disclosed herein. If the analyte of interest is a blood borne virus such as HIV, HBV, HCV, HSV-1 or HSV-2, EBV or CMV appropriate levels of the analytes may be purchased from a commercially available source (AcroMetrix Corporation).

The viral spike volume may be variable within the range of 1-50% of the total volume, depending on the viral load that was used for spiking. For example, if the total sample volume was 500 µL, the interference panel was spiked with a viral stock ranging from 0.5 to 250 µL, for a final volume of 500 µL for individual members of the inhibition panel. The desired volume should not exceed more than 50% of the total volume, as this may diminish the effective range of the potential interfering substance.

All interference panel members, including EDTA plasma, were spiked with an equal volume and copies of the desired analyte, so that the interference/non-interference claims of the extraction and assay system are properly verified.

In Table 2, HCV, the blood borne analyte of interest, was spiked into each panel member listed in Table 1. An equal volume of each panel member (0.5 mL) was spiked with an equal volume (0.5 mL) of HCV to give a total volume of 1.0 mL for each sample. Also, an equal amount of copies of the target analyte were added using a known titer value of 5E5 IU/mL, so that the interference/non-interference interpretation of the extraction and assay system were properly verified.

TABLE 2

Interference Panel Sample Preparation

| Panel Member | Volume of viral spike (mL) | Volume of panel member (mL) | Total volume of sample prep (mL) |
| --- | --- | --- | --- |
| EDTA Plasma | 0.5 | 0.5 | 1.0 |
| Haemolyzed Plasma (low) | 0.5 | 0.5 | 1.0 |
| Haemolyzed Plasma (mid) | 0.5 | 0.5 | 1.0 |
| Haemolyzed Plasma (high) | 0.5 | 0.5 | 1.0 |
| Heparinized Plasma | 0.5 | 0.5 | 1.0 |
| Lipemic Plasma | 0.5 | 0.5 | 1.0 |
| Icteric Plasma | 0.5 | 0.5 | 1.0 |

The analyte spike may be added directly to the inhibition panel member vials, or the inhibition panel members may be aliquoted into smaller volumes (additional vials not included) and then spiked with appropriate volumes of the analyte. The analyte spike volume was variable within the flexible range of 1% to 50% of the total volume, depending on the concentration that was used for spiking. For instance, if the total volume required for the initial extraction or assay procedure was 500 µL, the analyte spike volume may range from 0.5 µL to 250 µL. An appropriate volume of each member of the Inhibition Panel should then be added to reach the final volume of 500 µL.

The desired analyte volume should not exceed more than 50% of the total volume, as this will diminish the effective range of the potential interfering substances. The inhibition panel may be used more than once depending on the input volume requirements of the particular extraction or assay methodology utilized.

Example 8

Assay Evaluation

The panel members spiked with analyte of interest as shown in Tables 1 and 2 were then utilized for the different extraction systems with 1-3 replicas depending on the starting volume. Data in Table 3 shows the analysis of HCV spiked into the inhibition panel members, extracted via a commercial extraction system and analyzed within the reportable dynamic range of the assay (5E4 copies/mL) using a nucleic acid analyzer, such as the COBAS TaqMan® 48 HCV ASR.

The level of interference caused by the challenging panel member was quantified by comparison of either the delay in the threshold cycles (Ct's), or the decrease in the quantity of virus particles (using the EDTA plasma as optimal matrix) in the presence of the interfering substance.

Table 3 shows the inhibitory effect of Heparinized Plasma, Lipimic Plasma and Icteric Plasma compared to EDTA plasma, which served as non-inhibitory reference. The "Average Ct (cycle time)" was compared for each panel member to EDTA plasma. A one Ct delay represented approximately a 50% inhibition, meaning the titer could be underestimated by a factor of two. A two cycle delay would indicate a possible four fold underestimation. The three haemolyzed plasmas showed practically no inhibitory effect.

The inhibition panel can also be used to examine the function of QS (quantification standard), which is intended to monitor inhibition. Ideally, QS should be delayed by the same number of cycles as the target Ct. In this experiment it can be seen that a 7.9 cycle target Ct delay caused by heparin is mimicked by a 7.3 cycle delay of the QS, which still allowed reporting of a reasonably accurate target titer. This kind of experiment was useful to demonstrate the robustness of an assay in the presence of inhibitors.

TABLE 3

Performance of nucleic acid analyzer (COBAS TaqMan ®) 48 HCV ASR with HCV spiked into Interference Panel Members

| Panel Member | Average Ct (sample) | Ct Bias (sample) | Average Ct (QS) | Ct bias (QS) | Average Quantity | Quantity Bias |
|---|---|---|---|---|---|---|
| EDTA Plasma | 29.7 | 0.0 | 33.0 | 0.0 | 3.16E+04 | 0 |
| Haemolyzed Plasma (low) | 29.7 | 0.0 | 32.8 | −0.2 | 2.76E+04 | −4.00E+03 |
| Haemolyzed Plasma (mid) | 29.5 | −0.2 | 32.7 | −0.3 | 2.91E+04 | −2.53E+03 |
| Haemolyzed Plasma (high) | 29.8 | 0.1 | 33.0 | 0.0 | 2.74E+04 | −4.20E+03 |
| Heparinized Plasma | 37.6 | 7.9 | 40.3 | 7.3 | 1.04E+04 | −2.12E+04 |
| Lipemic Plasma | 32.6 | 2.9 | 35.1 | 2.1 | 1.99E+04 | −1.17E+04 |
| Icteric Plasma | 31.0 | 1.3 | 33.7 | 0.7 | 2.08E+04 | −1.09E+04 |

I claim:

1. A method for evaluating the performance of an analytical assay comprising:
    adding a known quantity of an analyte to members of an interference panel, wherein the members of the interference panel contain a known amount of a substance that may interfere with the analytical assay,
    performing the analytical assay on the members of the interference panel to obtain a measurement of the analyte in the members of the panel, and
    comparing the measurement of the analyte in the members of the panel with the known quantity of the analyte that was added to assess inhibition of the assay by the members of the interference panel.

2. The method of claim 1 wherein the comparison identifies substances in the members of interference.

3. The method of claim 1 wherein the analytical assay amplifies nucleic acids.

4. The method of claim 3 wherein the analytical assay is PCR.

5. The method of claim 1 wherein the analyte is a nucleic acid.

6. The method of claim 1 wherein the analyte is an antibody.

7. The method of claim 1 wherein the analyte is an antigen.

8. The method of claim 1, wherein the analyte is extracted from whole blood.

9. The method of claim 1, wherein the analyte is extracted from serum.

10. The method of claim 1, wherein the analyte is extracted from plasma.

11. The method of claim 1, wherein a member of the inhibition panel is comprised of haemolyzed blood having one or more discrete concentrations.

12. The method of claim 1, wherein one of the members of the inhibition panel is comprised of heparinized plasma.

13. The method of claim 1, wherein one of the members of the inhibition panel is comprised of lipemic plasma.

14. The method of claim 1, wherein one of the members of the inhibition panel is comprised of EDTA plasma.

15. The method of claim 1, wherein one of the members of the inhibition panel is comprised of icteric plasma.

16. The method of claim 1, wherein one of the members of the inhibition panel is a plurality of discrete concentrations of haemolyzed blood.

17. The method of claim 1 wherein the level of interference is quantified by comparison of a measurement of a reference plasma sample with the measurement of members of the inhibition panel.

18. The method of claim 1 wherein the assay measures a parameter.

19. The method of claim 1 wherein a measurement of inhibition by one or more of the panel members is quantified.

20. The method of claim 1 wherein the analyte is a blood derived analyate.

21. The method of claim 1 wherein the analyte is a blood borne analyte.

22. The method of claim 21 wherein the blood borne analyte is a blood borne virus.

23. The method of claim 21 wherein the blood borne virus is HIV, HBV, HCV, HSV1, HSV-2, EBV or CMV.

24. The method of claim 1, wherein at least one of the members of the inhibition panel is comprised of a blood derivative.

25. The method of claim 24, wherein at least one of the members of the inhibition panel is comprised of a whole blood derivative.

26. The method of claim 1, wherein the substance that may interfere with the analytical assay is selected from the group consisting of hemoglobin, lipids, bilirubin, and heparin.

* * * * *

UNITED STATES PATENT AND TRADEMARK OFFICE
CERTIFICATE OF CORRECTION

| | | |
|---|---|---|
| PATENT NO. | : 8,097,461 B2 | Page 1 of 1 |
| APPLICATION NO. | : 11/941017 | |
| DATED | : January 17, 2012 | |
| INVENTOR(S) | : Michael J. Eck | |

It is certified that error appears in the above-identified patent and that said Letters Patent is hereby corrected as shown below:

At column 12, Claim 20, line 61, replace "analyate" with --analyte--.

Signed and Sealed this
First Day of May, 2012

David J. Kappos
*Director of the United States Patent and Trademark Office*